(12) United States Patent
Sharek et al.

(10) Patent No.: US 9,194,748 B2
(45) Date of Patent: Nov. 24, 2015

(54) SYSTEM, METHOD AND COMPUTER SOFTWARE PRODUCT FOR DETECTION OF GROUND ANOMALIES USING DUAL-FILTER INFRARED IMAGING

(71) Applicant: LOCKHEED MARTIN CORPORATION, Bethesda, MD (US)

(72) Inventors: Patricia Skelley Sharek, Orlando, FL (US); Gene D. Tener, Oviedo, FL (US); Albert Ciullo, Orlando, FL (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 107 days.

(21) Appl. No.: 13/851,030

(22) Filed: Mar. 26, 2013

(65) Prior Publication Data

US 2013/0248715 A1    Sep. 26, 2013

Related U.S. Application Data

(60) Provisional application No. 61/615,432, filed on Mar. 26, 2012.

(51) Int. Cl.
| | |
|---|---|
| *G01J 5/02* | (2006.01) |
| *G01J 3/36* | (2006.01) |
| *G01J 5/60* | (2006.01) |
| *G01N 21/35* | (2014.01) |
| *G01J 3/12* | (2006.01) |

(52) U.S. Cl.
CPC .... *G01J 5/02* (2013.01); *G01J 3/36* (2013.01); *G01J 5/602* (2013.01); *G01J 2003/1213* (2013.01); *G01N 21/35* (2013.01)

(58) Field of Classification Search
CPC .............. G01J 5/02; G01J 5/602; G01J 3/36; G01J 2003/1213; F01N 21/35
See application file for complete search history.

(56) References Cited

U.S. PATENT DOCUMENTS

| | | | |
|---|---|---|---|
| 3,404,283 A * | 10/1968 | Stanfill, III et al. | ........... 250/226 |
| 2010/0226011 A1 | 9/2010 | Szapiel et al. | |
| 2010/0231716 A1 | 9/2010 | Klaerner et al. | |
| 2012/0033220 A1 * | 2/2012 | Kotidis et al. | ................. 356/445 |
| 2012/0098971 A1 * | 4/2012 | Hansen et al. | ................. 348/164 |
| 2012/0133775 A1 | 5/2012 | Treado et al. | |

* cited by examiner

*Primary Examiner* — Yara B Green
(74) *Attorney, Agent, or Firm* — Terry M. Sanks, Esq.; Beusse Wolter Sanks & Maire, PLLC

(57) ABSTRACT

A system including a sensor to receive scattered light from a scene in a thermal infrared spectral region, a Modified Integrated Thermal (MIT) band filter to acquire MIT band data within a thermal detection bandwidth, a sub-band filter to acquire a first sub-band data within a first sub-band bandwidth which is within the thermal detection bandwidth. The sub-band filter is a Reference band filter to capture Reference band data or a Reststrahlen band filter to capture Reststrahlen band data. The system also includes one or more processors configured to perform differencing of the MIT band data and the first sub-band data to compute a second sub-band data. The computed second sub-band data is Reference band data when the sub-band filter is the Reststrahlen band filter or the computed second sub-band data is Reststrahlen band data when the sub-band filter is the Reference band filter. A method and a computer software product are also disclosed.

20 Claims, 7 Drawing Sheets

SYSTEM, METHOD AND COMPUTER SOFTWARE PRODUCT FOR DETECTION OF GROUND ANOMALIES USING DUAL-FILTER INFRARED IMAGING

CROSS-REFERENCE TO RELATED APPLICATIONS

This application claims the benefit of U.S. Provisional Application No. 61/615,432 filed Mar. 26, 2012, titled "Dual-Filter LWIR Imaging for Detection of Anomalies in a Scene" and incorporated herein by reference in its entirety.

BACKGROUND

Embodiments relate to detection of anomalies and, more particularly, to use of infrared filters for detection of anomalies in a scene while stationary and/or on-the-move.

Deployed troops can be endangered by improvised explosive devices (IEDs). Most IEDs have some element (ordnance, pressure plates, wires, etc.) on the surface, near-surface or deeply buried in the ground and/or ground disturbance resulting from human or mechanical emplacement activity. The current state of the art (SOA) of detection systems for sensing disturbed ground include laser spectroscopy, broadband imaging and hyperspectral imaging over the visible and infrared spectrum.

The emissivity signature of silicates in soil, known as the Reststrahlen effect, is found in the long wave infrared (LWIR) spectrum, roughly between 8.2 µm and 9.4 µm. As known in the art, the emissivity of a material (usually written ϵ or e) is the relative ability of the surface of the material to emit energy by radiation, and is expressed as the ratio of energy radiated by the material to the energy that would be radiated by an ideal black body at the same temperature. Use of a LWIR hyperspectral approach is one known method used to detect spectral phenomena associated with the Reststrahlen effect. While the hyperspectral approach is capable of capturing the Reststrahlen signature, it is not optimum for providing thorough integrated thermal imagery that is important to situational awareness and the discovery of local thermal variations due to surface and near-surface emplacements and changes in soil character, density and moisture related to deeper buried articles. A hyperspectral approach may also be susceptible to impacts from shifts in the spectral content due to unique character of the soils. These limitations are due, in part, to the narrow bandwidth involved with the hyperspectral approach which has a low signal-to-noise ratio ("SNR").

SUMMARY

Embodiments relate to a system, method and computer software product for detection of an anomaly in a scene while stationary and/or on-the-move with dual-filter infrared. The system comprises an image sensor configured to receive scattered light from a scene in a thermal infrared spectral region. The system also comprises a Modified Integrated Thermal (MIT) band filter to acquire MIT band data within a thermal detection bandwidth. The system also comprises a sub-band filter to acquire a first sub-band data within a first sub-band bandwidth which is within the thermal detection bandwidth, the sub-band filter is a Reference band filter to capture Reference band data or a Reststrahlen band filter to capture Reststrahlen band data. The system also comprises one or more processors configured to perform differencing of the MIT band data and the first sub-band data to compute a second sub-band data, the computed second sub-band data is Reference band data when the sub-band filter is the Reststrahlen band filter or the computed second sub-band data is Reststrahlen band data when the sub-band filter is the Reference band filter.

The method comprises acquiring, by a Modified Integrated Thermal (MIT) band filter, MIT band data within a thermal detection bandwidth of a thermal infrared spectrum, and acquiring, by a sub-band filter, a first sub-band data within a first sub-band bandwidth which is within the thermal detection bandwidth. The method further comprises performing, by one or more processors, differencing of the MIT band data and the first sub-band data to compute a second sub-band data wherein the sub-band filter comprises a Reference band filter to capture Reference band data or a Reststrahlen band filter to capture Reststrahlen band data and the computed second sub-band data is Reference band data when the sub-band filter is the Reststrahlen band filter or the computed second sub-band data is Reststrahlen band data when the sub-band filter is the Reference band filter.

The computer software product comprises a non-transitory processor readable storage medium comprising executable computer program product which further comprises computer software code that, when executed on one or more processors, causes the one or more processors to process Modified Integrated Thermal (MIT) band data within a thermal detection bandwidth of a long wave infrared band spectrum from a MIT band filter. The one or more processors are also caused to process a first sub-band data within a first sub-band bandwidth which is within the thermal detection bandwidth from a sub-band filter, the sub-band filter is configured to be a Reference band filter to capture Reference band data or a Reststrahlen band filter to capture Reststrahlen band data. The one or more processors are also caused to perform differencing of the MIT band data and the first sub-band data to compute a second sub-band data wherein the computed second sub-band data is Reference band data when the sub-band filter is the Reststrahlen band filter or the computed second sub-band data is Reststrahlen band data when the sub-band filter is the Reference band filter.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1A:
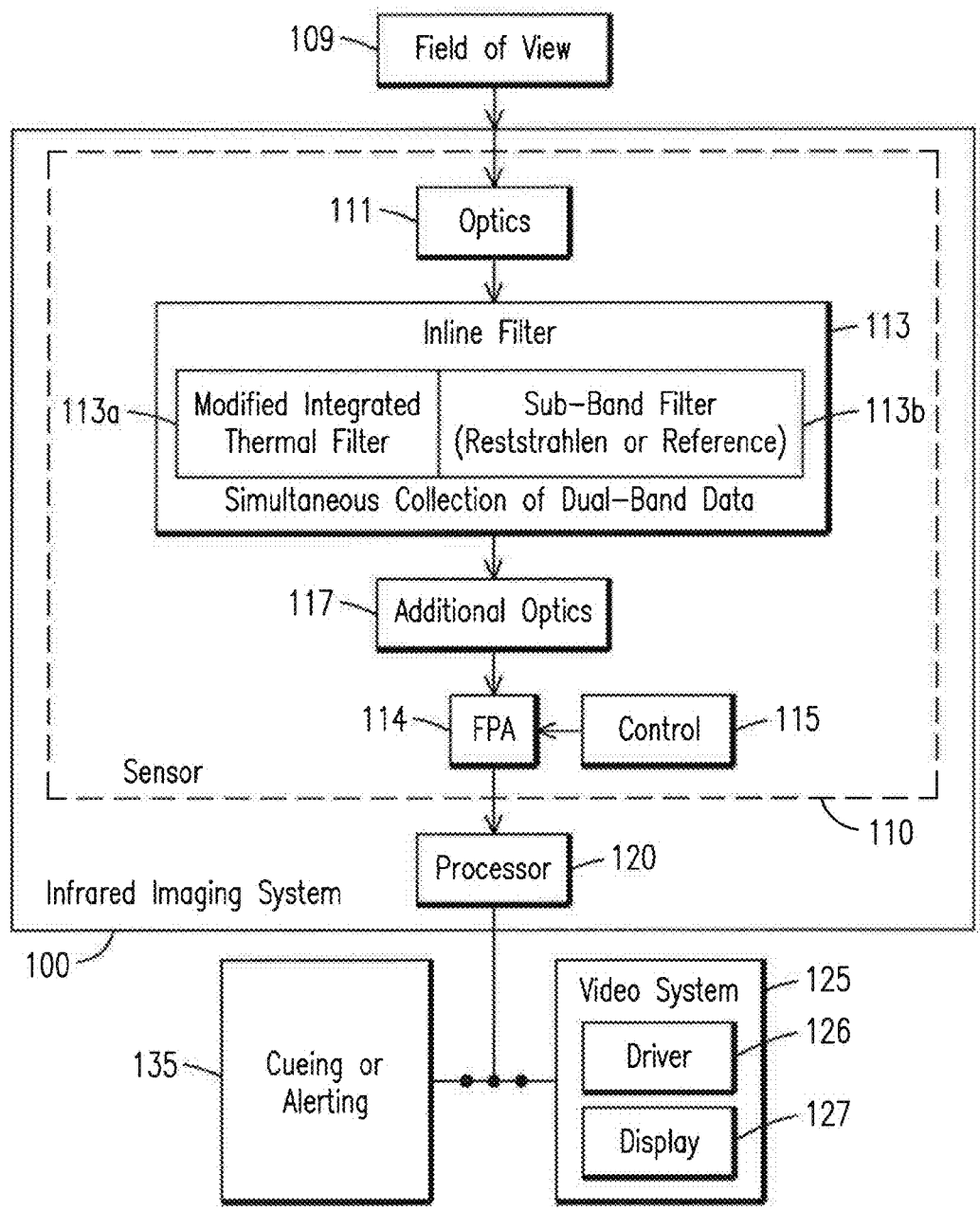
FIG. 1A shows a block diagram illustrating a system with an inline filter in accordance with one or more embodiments.

Embodiments are described with reference to the attached figures, wherein like reference numerals, are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Embodiments include use of infrared imaging using cooled or un-cooled cameras for detecting a local variation to identify one or more anomalies in or on the ground that are attributable to surface, near-surface or subsurface emplacements or activity, or environmentally induced conditions associated with human or mechanical activity. As used herein, "ground" is broadly defined to include surfaces of the earth, whether comprising small particles (e.g., sand) or large particles (e.g., gravel), whether or not including vegetation thereon, and/or whether being manmade or naturally formed. As used herein, "imagery" refers to electronic image data, which can optionally be visibly displayed on a suitable display device. As used herein, "inline filtering" refers to the positioning of a filtering device in the optical path between the scene/field of view and the detector, such as for cooled detector embodiments where as the filter device is outside a dewar in warm space, or cooled space inside the dewar or in close proximity to the detector. For a filtering system used in conjunction with a cooled detector, whether inline or insertion filtering, the filter can be positioned outside a dewar (warm space), or inside a dewar (cooled space), wherein the filter may be in close proximity to a focal plane, intermediate focal plane or otherwise located in the optical path. For a filter used in conjunction with an uncooled detector, whether inline or insertion filtering, the filter can be positioned in close proximity to a focal plane, intermediate focal plane or otherwise located in the optical path. As used herein, "dual-filtering" is configured so that portions of the filter transmits specific bands and blocks other bands of the coincident energy and thereby allows simultaneous or sequential collection of data from the multiple bands. Data is acquired in a Reststrahlen band, Reference band and a Modified Integrated Thermal (MIT) band for analysis and imaging of spectral and/or thermal properties to identify emplacements and activities of interest, as shown in FIGS. 4A 4B, 4C, 4D and 5, as will be described in more detail below. As used herein and as shown in FIGS. 2, 4A, 4B, 4C, 4D and 5, C/S layer stands for single layer/homogeneous soil, C/C layer stands for composite (non-homogeneous) soil (i.e. composition varied with depth), U stands for undisturbed soil, and D for disturbed soil. As used herein, image registration or "registering" is the process of transforming different images into one coordinate system. As used herein, a "sub-band" is defined herein as a band contained within the MIT band.

Figure 2:
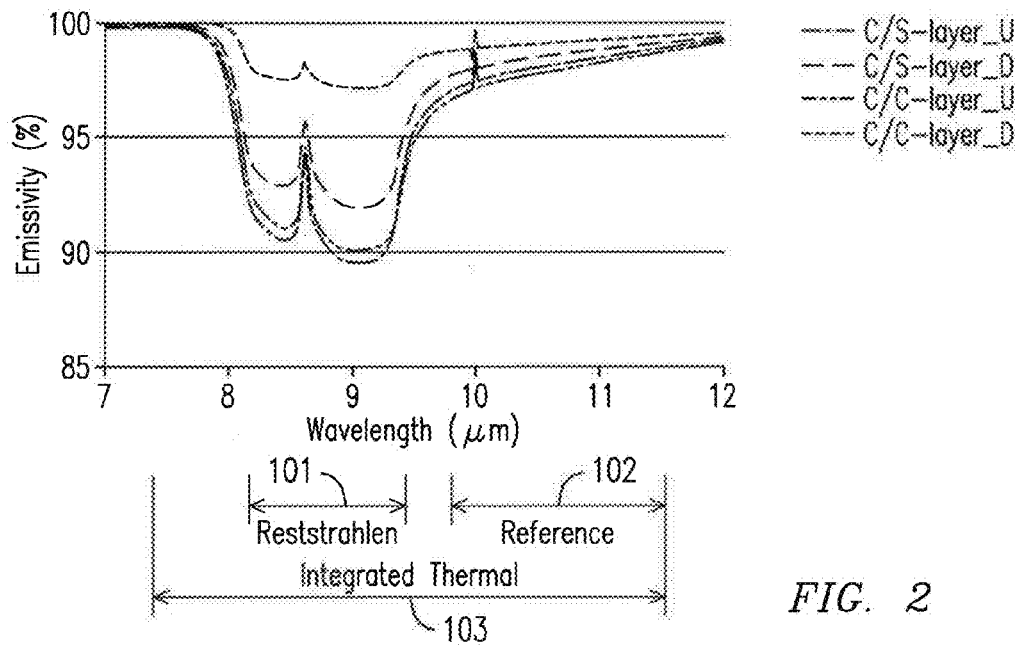
FIG. 2 shows a plot illustrating emissivity vs. wavelength of the Reststrahlen Effect on Disturbed Soil in combination with a Reststrahlen band, Reference band and typical Integrated Thermal band.

FIG. 2 shows a plot illustrating emissivity vs. wavelength of the Reststrahlen Effect on Disturbed Soil in combination with a Reststrahlen band, Reference band and Integrated Thermal band. The plot is based on emissivity versus wavelength. Data from these three bands allows analysis and imaging of Reststrahlen and thermal properties in a scene. The location of the Reststrahlen band within the long wave infrared band spectrum is essentially fixed but a range of the Reststrahlen band may vary based on the environment.

Thermal imagery may be captured with a single dedicated filter. In the illustration of FIG. 2, the thermal imagery is captured using a filter having a bandwidth corresponding to an Integrated Thermal band 103. As illustrated, the Integrated Thermal band 103 can stretch from a lower bound to an upper bound of the LWIR sensor (i.e. typically from 7.6 µm and upwards to about 14 µm), and capture imagery over the full performance band of the camera.

Spectral imagery, in accordance with FIG. 2, is built using two bands that are co-registered together and registered with the Integrated Thermal band 103. In the illustration of FIG. 2, the co-registration of the Reststrahlen band 101 and Reference band 102 are fundamental to the analysis of the Reststrahlen effect. Comparison of the Reference band 102 (a band which does not encompass the Reststrahlen feature) data and Reststrahlen band 101 (a band which encompasses the Reststrahlen feature) data enables separation of thermal influences from the Reststrahlen phenomenology of silicates that are attributable to changes (disturbance) in soil or ground. The imagery is registered pixel-to-pixel to determine localized Reststrahlen evidence of disturbed ground (e.g., soil) in a scene from which imagery is assembled.

Imagery must be accurately registered, to sub-pixel accuracy, between the sequentially obtained spectral band images to accurately detect phenomenology. Implementing this sequential filtering approach on-the-move, from a vehicle in an operationally relevant environment, is generally plagued with registration errors that impair image quality and the ability to identify subtle variations in Reststrahlen and thermal signatures needed for analysis of scene content and the detection of anomalies. The vehicle may include one of a ground vehicle, air-borne vehicle, and lighter-than-air vehicle.

We have determined that such on-the-move data has revealed that significant spatial changes (many pixels) occur between acquisition of each of the sequential bands of data due to significant switching time between filters. The spatial shift varies between spectral images depending on optical flow, with increasing pixel shift (optical flow) as pixels deviating from the line of sight (LOS) in the direction of travel. Further, complicating registration occurs as a vehicle turns since some or all pixels will shift between the spectral images. Additionally, when moving objects are introduced in the scene, even pixels along the LOS in the direction of travel will shift between collection of bands, even in cases where the background may be static. Compensating for relative image motion between pixels from various sources of relative motion is problematic using this sequential filtering approach. Moreover, the more successive bands collected, the longer lapse of time between the first and last spectral images, and the greater the impact on registration further compound the complications.

Known inline filtering generally reduces resolution. More specifically, the more band filters used, the less resolution may be realized. By way of a non-limiting example, if an image has 900 pixels, a three-band inline filter will capture 300 pixels each. Thus, the resolution is generally reduced by a number of band filters used simultaneously.

FIG. 1A shows a block diagram illustrating a system with an inline filter in accordance with one or more embodiments. An infrared imaging system 100 may comprise an inline dual-band filter 113 which may be used for detecting emplacements and emplacement activity in an interrogated field of view 109. The system 100 may be considered a passive imaging system as it does not require a separate light source. The system 100 may comprise an image sensor 110 comprising optics 111 that provides an aperture for system 100 and collects and focuses light from the field of view 109. The image sensor 110 may comprise the inline dual-band filter 113 configured to simultaneously collect dual-band data. The optics 111 is optically coupled to an inline dual-band filter 113. The inline dual-band filter 113 may comprise a Modified Integrated Thermal (MIT) band filter 113a and a sub-band filter 113b. The sub-band filter 113b includes a Reststrahlen band filter or a Reference band filter. The inline dual-band filter 113 being configured to provide simultaneous collection of dual-band data where the MIT band filter 113a is configured to capture MIT data in a thermal detection bandwidth within the thermal infrared band spectrum, as will be described in more detail in relation to FIGS. 4A, 4B, 4C, 4D and 5. The thermal infrared band spectrum includes at least long wave infrared (LWIR).

Returning again to the system 100, the imaging sensor 110 may use additional optics 117 as shown between the output of inline dual-band filter 113 and a detector array shown as a focal plane array (FPA) 114. Although not shown, the FPA 114 may be within a cryogenically cooled dewar. The FPA 114 is an image sensing device which may comprise an array of light-sensing pixels at a focal plane of a lens.

Associated with the FPA 114 is a control block 115 that comprises control electronics, such as but not limited to one or more processors. The control block 115 may generate at least one control signal (e.g., control voltages) to control the operation of the FPA 114 or other detector array. In an embodiment, the FPA 114 may comprise complementary metal-oxide semiconductor (CMOS) elements and the control block 115 may generally be formed on the same substrate having a semiconductor surface (e.g., a silicon chip) that generates the on-chip control signals (e.g., voltage pulses) used to control the operation of the FPA 114.

The infrared imaging system 100 may comprise one or more processors 120, such as, but not limited to, a digital signal processor (DSP) or microcomputer. The one or more processors 120 may be coupled to receive and process the at least one electrical signals provided by the FPA 114. The one or more processors 120 may provide data processing to implement electronic differencing of the MIT band data and sub-band data. An output of the one or more processors 120 is shown optionally coupled to a video system 125 comprising video driver 126 which is coupled to a video display 127, such as a video screen that provides a viewable color or black and white image. The output of the one or more processors 120 may also be coupled to the cueing or alerting block 135, that can be used to display, cue or alert an operator(s) to emplacements in the ground, as well as local variations in ground (soil) attributable to living or mechanical activity.

In an embodiment, the cueing or alerting block 135 may be used in conjunction with change detection. The cueing or alerting block 135 may provide heightened situational awareness over a field of view.

In an embodiment, instead of simply alerting through the display 127, the system 100 may be integrated into a control system of a vehicle. If an alert is provided, the system 100 may signal the control system of the vehicle to take a particular action, such as, but not limited to, stop, change paths, etc.

The inline dual-band filtering of the system 100, as illustrated in FIG. 1A (with warm or cooled space) may eliminate or reduce registration problems in various types of sensor architectures including scanning, staring and step-stare arrays. The simultaneous collection of the dual-band data using inline dual-band filtering in various sensor architectures may overcome temporal issues that undermine registration. In an embodiment, inline dual-band filtering by the inline dual-band filter 113 may be implemented on or in close proximity to a staring FPA. As an example, spatial correlation between pixels for a "checkerboard" two-filter pattern is better than a known triad pattern of 3-filters (Reststrahlen filter, Reference filter, Integrated Thermal filter).

In an embodiment, registration problems may be eliminated or reduced when an inline dual-band filter 113 is implemented in a scanning FPA architecture, such as a Standard Advanced Dewar Assembly (SADA) sensor, where the temporal correlation between odd and even scan rows is very good (time between odd and even rows is very short relative to scene motion).

In an embodiment, inline implementation of the inline dual-band filter 113 may be simplified in such scanning array architectures, due to the physical separation between odd and even rows of pixels. By increasing the available pixel-to-band ratio, the inline dual-band filtering embodiments may improve the resolution (and/or FOV) for various sensor architectures as compared to three-filter methods for acquiring Reststrahlen band 101, Reference band 102 and Integrated Thermal band data 103.

Figure 1B:
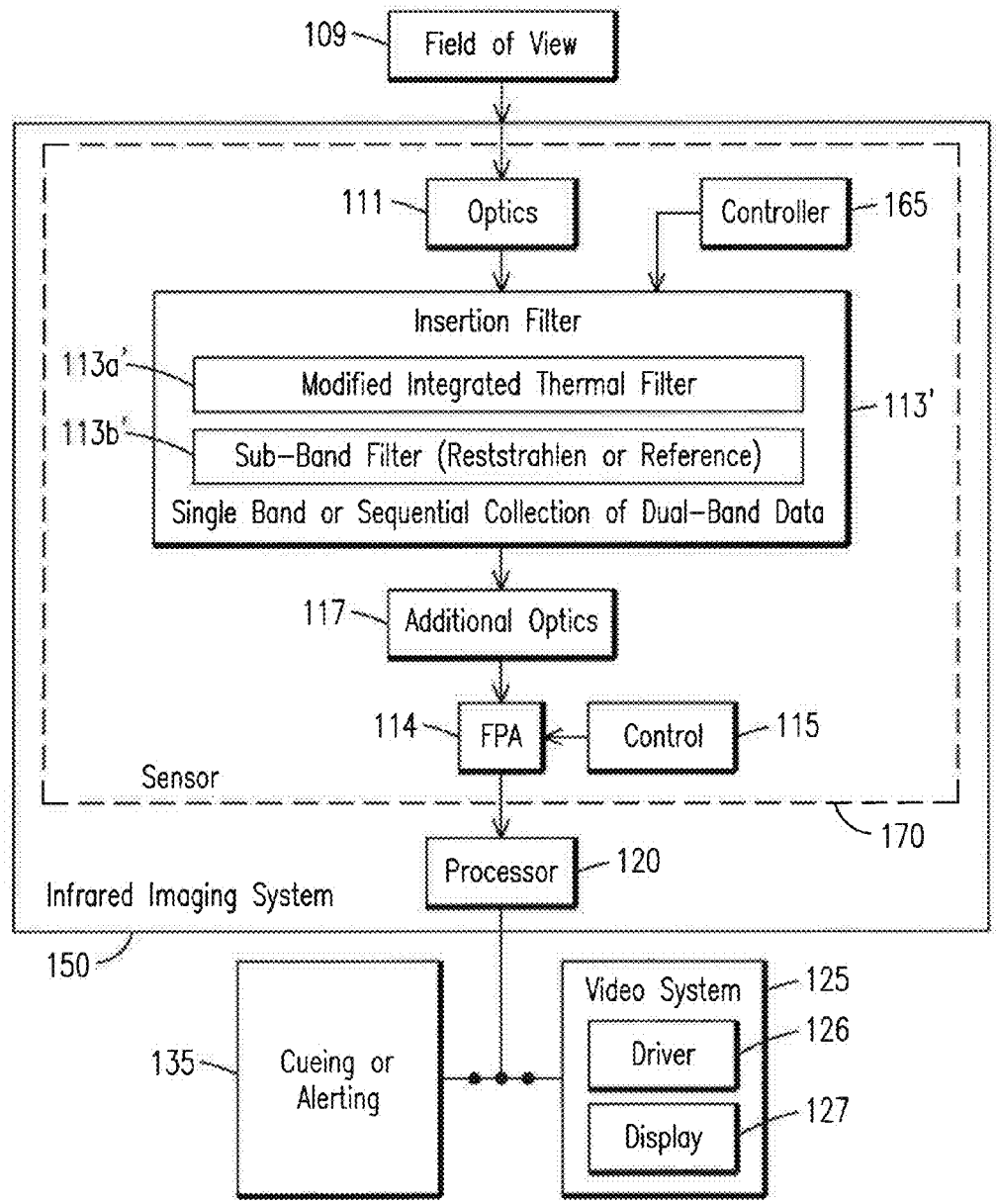
FIG. 1B shows a block diagram illustrating a system with an insertion filter in accordance with one or more embodiments.

FIG. 1B shows a block diagram illustrating a system with an insertion filter in accordance with one or more embodiments. An infrared imaging system 150 is shown having an insertion filter 113' to detect Reststrahlen effect and thermal phenomenology. The insertion filter 113' may be static within the system 150. The sensor 170 of system 150 includes a controller 165 that sends control signals to actuate a device (e.g., filter wheel or rocker) that inserts, in a filter insertion phase, and removes, during a filter removal phase, the MIT band filter 113a' and sub-band filter 113b' in and out of the optical path. The sub-band filter 113b' includes a Reference band filter to capture Reference band data or a Reststrahlen band filter to capture Reststrahlen band data. The MIT band filter 113a' is configured to capture MIT data in a thermal detection bandwidth within the thermal infrared band spectrum, as will be described in more detail in relation to FIGS. 4A, 4B, 4C, 4D and 5. Otherwise, the system 150 is analogous to system 100 and like components previously described have like reference numerals and will not be further described.

The insertion filtering (warm or cooled space) embodiments, illustrated in FIG. 1B may also reduce registration issues in various types of sensor architectures including scanning, staring and step-stare arrays. Use of the dual-band approach significantly reduces the opto-mechanical and dynamic complexities encountered with insertion filtering using the known three filter method while still providing essential spectral and integrated thermal data with maximum resolution.

In an embodiment, inline dual-band filtering by the inline dual-band filter 113 may be implemented in a step-stare architecture, in which a mirror may step a camera or plurality of cameras containing a plurality of detectors that form a composite focal plane array. The dual-band filter may be implemented on or in close proximity to each focal plane.

As a non-limiting example, the insertion filter 113' may include a filter wheel implementation, where the respective filters (MIT band filter 113a' and sub-band filter 113b') can be constructed neighboring each other on both sides. The filter wheel implementation may eliminate the lapse of time associated with passage over a third band in continuous uniform-directional motion. Similarly, dual-band approach reduces complexity in other perceived techniques to insert and remove filters in the optical path of a sensor.

In an embodiment, the filter wheel implementation may include one or more MIT band filters and one or more sub-band filters in an alternating pattern.

In an embodiment, the insertion filter 113 may provide a sequential collection of alternating MIT band filtering followed by the sub-band filtering of one of the Reststrahlen band 101 and Reference band 206 or 216a and 216b.

In the embodiments of FIGS. 1A and 1B, dual-band filters are provided. The dual-band filters include the MIT band filter and a sub-band filter. In an embodiment, the dual-band filters may include two sub-band filters such as a Reststrahlen band filter and a Reference band filter to acquire Reststrahlen band data and Reference band data. In such an embodiment, the MIT band data is computed or extrapolated using differencing as described later.

Figure 3:
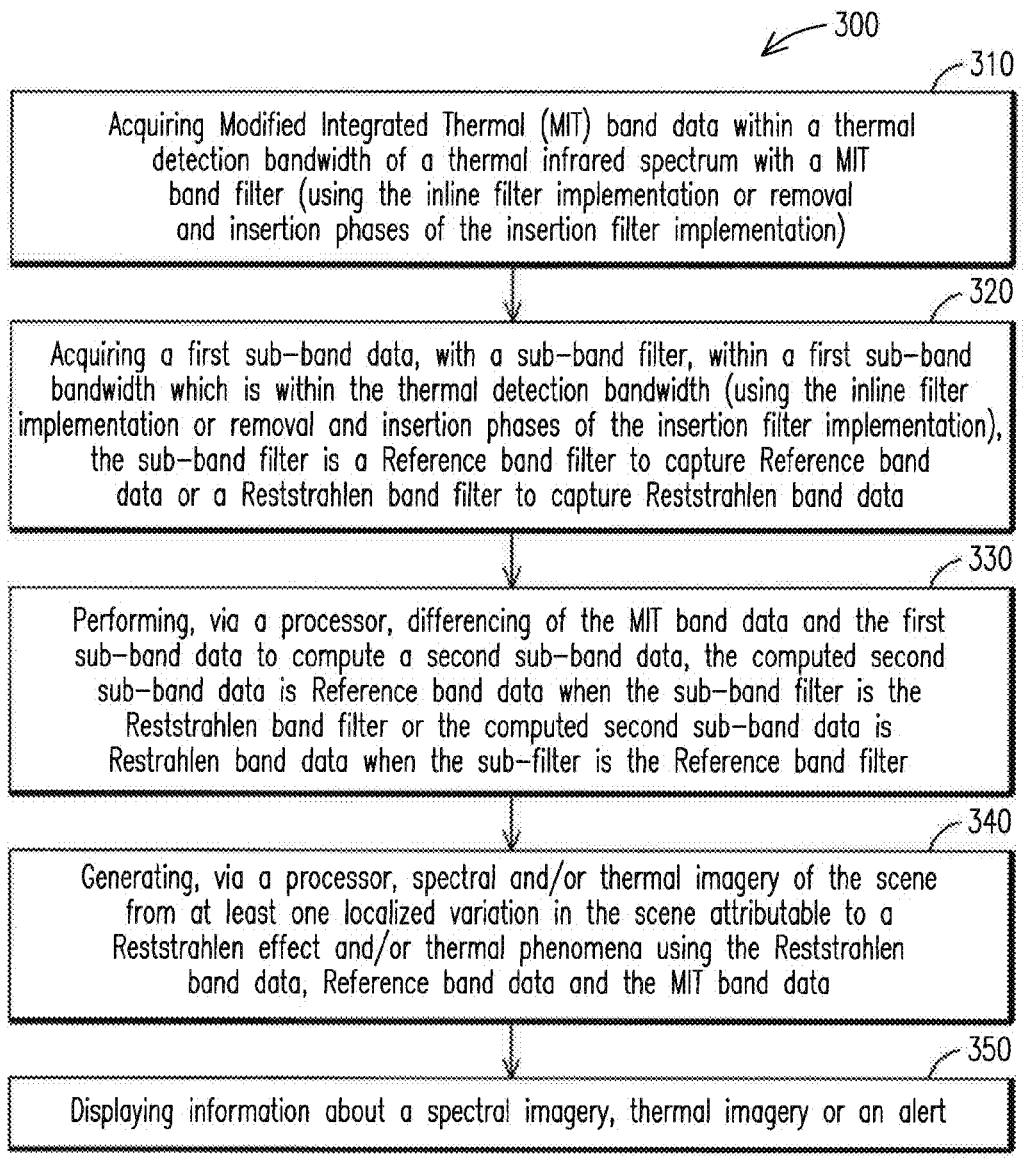
FIG. 3 shows a flowchart illustrating a method in accordance with one or more embodiments.

FIG. 3 shows a flowchart illustrating a method in accordance with one or more embodiments. The method 300 comprises acquiring MIT band data within a thermal detection bandwidth of a thermal infrared spectrum with a MIT band filter (e.g., 113a or 113a' of FIGS. 1A and 1B, respectively), at 310, using the inline filter implementation or removal and insertion phases of the insertion filter implementation. During the removal and insertion phases, a MIT band filter is inserted into the optical path. Hence, a sub-band filter is removed from the optical path and then reinserted in the optical path.

The method 300 further comprises acquiring a first sub-band data, with a sub-band filter (e.g., 113b or 113b' of FIGS. 1A and 1B, respectively), within a first sub-band bandwidth which is within the thermal detection bandwidth of the MIT band filter, at 320, using the inline filter implementation or removal and insertion phases of the insertion filter implementation. During the removal and insertion phases, a sub-band filter is inserted into the optical path. Hence, a MIT band filter is removed from the optical path and then reinserted in the optical path. The sub-band filter 113b or 113b' includes a Reference band filter to capture Reference band data or a Reststrahlen band filter to capture Reststrahlen band data.

The method 300 also comprises performing, via a processor 120, differencing of the MIT band data and the first sub-band data to compute a second sub-band data. Accordingly, the computed second sub-band data is Reference band data when the sub-band filter is the Reststrahlen band filter or Reststrahlen band data when the sub-band filter is the Reference band filter, at 330.

Figure 4A:
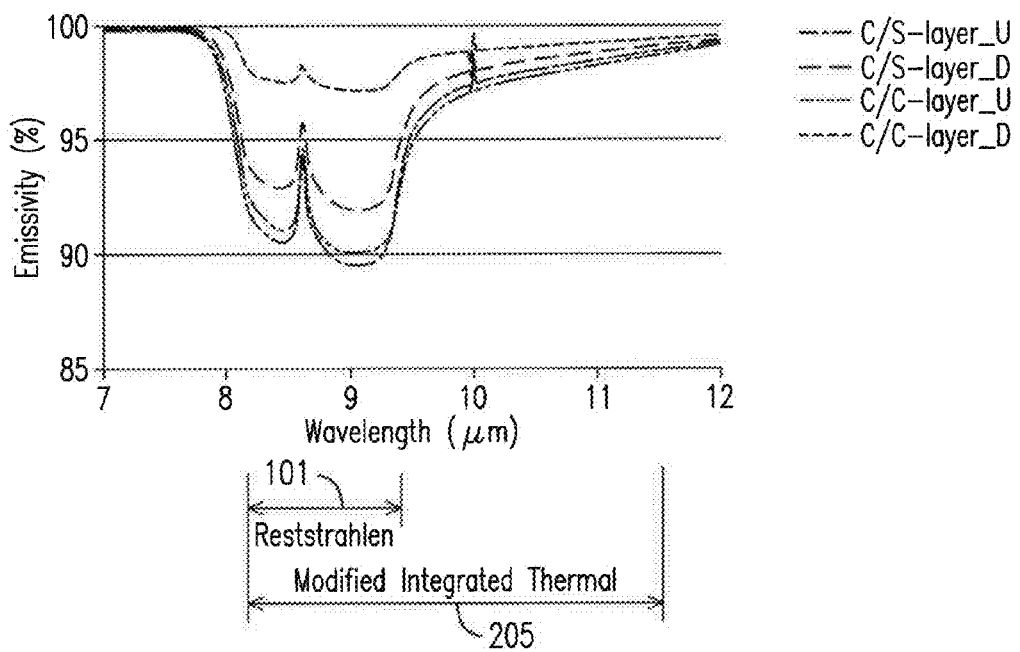
FIG. 4A shows a plot illustrating emissivity vs. wavelength of the Reststrahlen Effect on Disturbed Soil in combination with the Reststrahlen band and a Modified Integrated Thermal band in accordance with one or more embodiments.

The method 300 may further comprise generating, via a processor 120, spectral or thermal imagery of the scene from at least one localized variation in the scene attributable to a Reststrahlen effect or thermal phenomena, at 340. The method 300 may further comprise displaying information about a spectral imagery, thermal imagery and/or an alert, at 350. The Reststrahlen effect or thermal phenomena are determined based on the Reststrahlen band data, the Reference band data and the MIT data wherein the Reststrahlen band data or the Reference band data is computed while the other is acquired/captured by a sub-band filter. FIG. 4A shows a plot illustrating emissivity vs. wavelength of the Reststrahlen Effect on Disturbed Soil in combination with the Reststrahlen band and a MIT band. The plot is based on emissivity versus wavelength. The two bands filtered by the inline dual-band filter 113 or the insertion filter 113' are the Reststrahlen band 101 and the MIT band 205. The data collected from filtering allows analysis and imaging of Reststrahlen properties of ground and thermal properties in a scene. In this embodiment, the Reference band data may be computed or extrapolated with the one or more processors 120 by employing electronic differencing between the Reststrahlen data captured in the Reststrahlen band 101 and the MIT data captured in the MIT band 205.

In one or more embodiments described herein, although the location of the Reststrahlen band is essentially fixed, by way of non-limiting example as shown in FIGS. 4B, 4C, 4D or 5, the Reference band may be at any location within the thermal infrared band spectrum where there is essentially exclusive of Reststrahlen band data. Furthermore, the range of the Reference band may vary based on the thermal detection bandwidth of the MIT band 205, 205' or 508.

In an embodiment, the method may include acquiring first and second sub-band data (e.g. Reststrahlen band data and Reference band data) and computing or extrapolating the MIT band data.

Figure 4B:
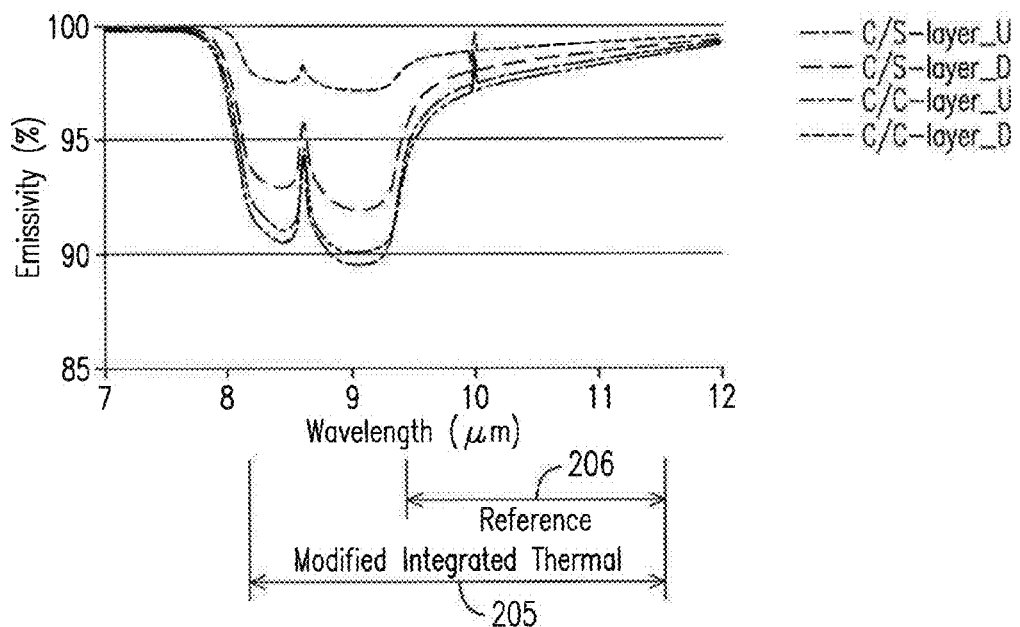
FIG. 4B shows a plot illustrating emissivity vs. wavelength of the Reststrahlen Effect on Disturbed Soil in combination with a Reference band and the Modified Integrated Thermal band in accordance with one or more embodiments.

FIG. 4B shows another plot illustrating emissivity vs. wavelength of the Reststrahlen Effect on Disturbed Soil in combination with the Reference band and the MIT band. The plot is based on emissivity versus wavelength. The two bands filtered are the Reference band 206 and the MIT band 205. The data collected may allow for analysis and imaging of Reststrahlen properties of ground and thermal properties in a scene. In this embodiment the Reststrahlen band data is computed or extrapolated by electronic differencing, with the one or more processors 120, from the Reference data captured from the Reference band 206 and the MIT data of the MIT band 205.

In an embodiment, the thermal detection bandwidth includes the MIT band 205. In an embodiment, the MIT band 205 may include a portion of, full or nearly full LWIR band spectrum.

In an embodiment, the MIT band 205 may include a first portion of the LWIR thermal band spectrum that overlaps with the Reststrahlen band 101 such that a leading edge of the MIT band coincides with the leading edge of the Reststrahlen band 101, as best seen in FIG. 4A. The MIT band may further include a second portion extending from the leading edge of the Reference band 206 (coinciding with a trailing edge of the Reststrahlen band 101) to a trailing edge of the MIT band such that the trailing edge of the MIT band coincides with a trailing edge of the Reference band 206 or a trailing edge near to, or in proximity to a trailing edge of the LWIR thermal band spectrum.

In an embodiment, the MIT band may include the first portion and the second portion of the thermal infrared band spectrum such that there is no gap between the first portion and the second portion.

In an embodiment, the Reference band filter is configured to or capable of capturing the full bandwidth of the thermal detection bandwidth except that portion of the Reststrahlen band 101 overlapping the thermal detection bandwidth.

In an embodiment, the Reference band filter has a band 206 which overlaps the MIT band 205 but does not overlap the Reststrahlen band 101; is configured to have a leading edge that corresponds to the trailing edge of the Reststrahlen band 101, as seen in FIG. 4B; and is configured to have a trailing edge correspond to the trailing edge of the MIT band 205.

Figure 4C:
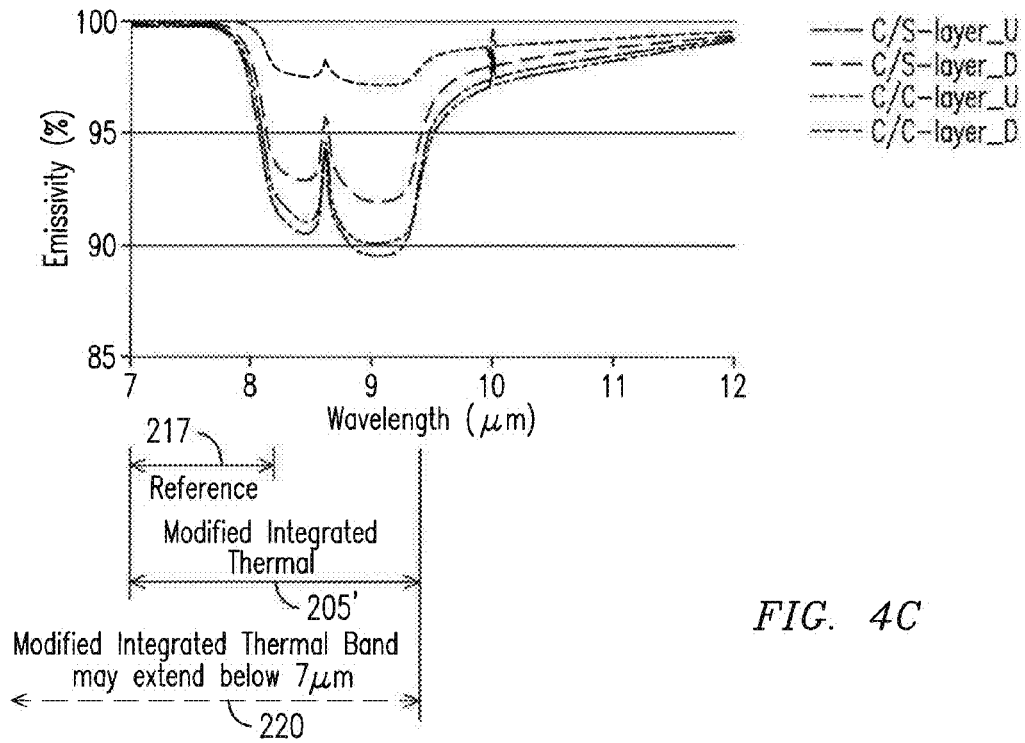
FIG. 4C shows a plot illustrating emissivity vs. wavelength of the Reststrahlen Effect on Disturbed Soil in combination with another Reference band and another Modified Integrated Thermal band in accordance with one or more embodiments.

FIG. 4C shows a plot illustrating emissivity vs. wavelength of the Reststrahlen Effect on Disturbed Soil in combination with another Reference band and another Modified Integrated Thermal band. The two bands filtered are the Reference band 217 and the MIT band 205'. The data collected may allow for analysis and imaging of Reststrahlen properties of ground and thermal properties in a scene. In this embodiment the Reststrahlen band data is computed or extrapolated by electronic differencing, with the one or more processors 120, from the Reference data captured from the Reference band 217 and the MIT data of the MIT band 205'.

In an embodiment, the Reference band filter has a band 217 which overlaps the MIT band 205' but does not overlap the Reststrahlen band 101. The MIT band 205' may include a beginning of the thermal infrared band spectrum as its leading edge, with a trailing edge that coincides with the trailing edge of the Reststrahlen band 101. The Reference band 217, as seen in FIG. 4C, has a leading edge that coincides with the beginning of the LWIR band spectrum and the MIT band 205', and a trailing edge which coincides with the leading edge of the Reststrahlen band 101.

In the embodiment of FIG. 4C, the leading edge of the Reference band 217 and the leading edge of the MIT band 205' are shown to have a cut-on of approximately 7 µm. In an embodiment, the MIT band 205' and the Reference band 217 may extending below the 7 µm cut-on into the medium-wave infrared (MWIR) thermal spectrum as represented by the dashed line 220, representing the bandwidth where the cut-on is below 7 µm.

Figure 4D:
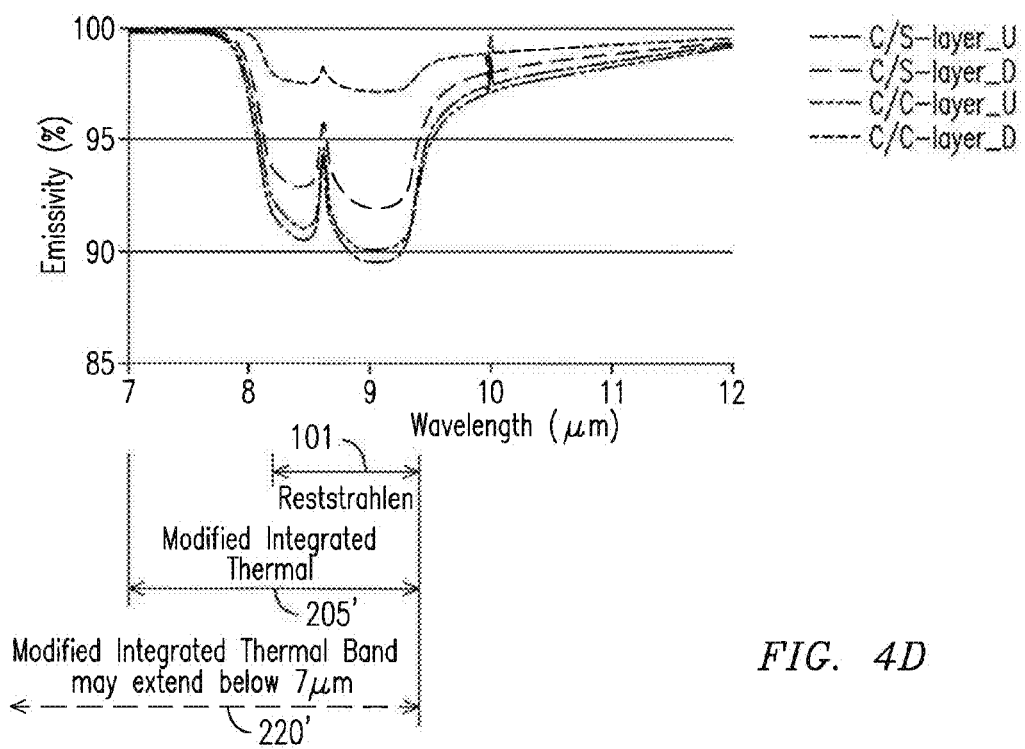
FIG. 4D shows a plot illustrating emissivity vs. wavelength of the Reststrahlen Effect on Disturbed Soil in combination with the Reststrahlen band and the another Modified Integrated Thermal band in accordance with one or more embodiments.

FIG. 4D shows a plot illustrating emissivity vs. wavelength of the Reststrahlen Effect on Disturbed Soil in combination with the Reststrahlen band and the another Modified Integrated Thermal band in accordance with one or more embodiments. With respect to the illustration of FIG. 4C, when the Reference band filter is used to acquire the Reference band data, the Reststrahlen band data is then computed. In relation to FIG. 4D, system may be configured to acquire the Reststrahlen band data within the Reststrahlen 101 using a Reststrahlen band filter and acquire the MIT band data in MIT band 205' and compute or extrapolate the Reference band data.

In the embodiment of FIG. 4D, the leading edge of the MIT band 205' is shown to have a cut-on of approximately 7 µm. In an embodiment, the MIT band 205' may extend below the 7 µm cut-on into the medium-wave infrared (MWIR) thermal spectrum as represented by the dashed line 220', representing the bandwidth where the cut-on is below 7 µm.

By way of a non-limiting example, the Reststrahlen band 101 may be within a range from 8.2 µm±0.2 µm to 9.4 µm±0.2 µm, and providing a bandwidth of at least 1 µm. Thus, using this non-limiting example, Reference band 206 (FIG. 4B) has a leading edge close to a trailing edge of the Reststrahlen band (i.e. 9.8 µm±0.2 µm) and an upper limit within the camera spectrum of 11.0 µm or greater. Furthermore by way of a non-limiting example, the MIT band data may be modified so that it is defined herein as 8.2 µm±0.2 µm to the optimized upper limit within the camera spectrum (11.0 µm or greater). By way of a non-limiting example, the LWIR band spectrum roughly extends to 14 µm, so the trailing edge of the MIT band filter 113a or 113a', as modified, and the Reference band filter may be selected within that range based on design factors that include maximization of the Reststrahlen signature, and maximization of the signal-to-noise ratio (SNR).

Acquiring the MIT band data generally involves using a long pass thermal filter (or passband filter depending on the camera cut-off). By way of a non-limiting example, the MIT band filter 113a or 113a' may have a leading transmission edge at 8.2 µm±0.2 µm, and a bandwidth of at least 2.6 µm. The 8.2 µm±0.2 µm cut-on may be selected because it is the leading edge of the Reststrahlen signature. The MIT band may be configured to cut-on at 8.2±0.2 µm. This cut-on of the MIT band has been found to eliminate the dependency on a third filter to acquire spectral imagery while still providing high signal-to-noise thermal imagery. Electronic differencing of data from the MIT band filter, as described herein, allows computing or extrapolating Reference band data if used in conjunction with a Reststrahlen band filter or computing or extrapolating Reststrahlen band data if used in conjunction with a Reference band filter with a leading edge near the trailing edge of the Reststrahlen signature.

The Reststrahlen range disclosed above may be varied or modified for different environments or scenes, and/or modified for optimizing for the environment or scene. Accordingly, the MIT band and the Reference bands may be also varied based on the Reststrahlen variations, the thermal detection bandwidth or the environment.

The MIT band filter, as modified, enables a two-band design that does not sacrifice high signal-to-noise in the thermal detection band, for detection of subtle variations in localized thermal profiles and overall situational awareness, in the pursuit of overcoming registration issues. The relationship between energy and wavelength ($\lambda$) is defined by Planck's constant ($h$), which is used to describe the size of energy quanta. $E=hc/\lambda=hv$, by where v is the frequency and c is the speed of light. Integrating over a relatively larger energy window, such as at least 2.6 µm provides a more robust signal and higher SNR.

Disclosed embodiments recognize a higher SNR can be realized by integration of the signal over a larger bandwidth.

$$SNR = \frac{\text{signal electrons}}{\text{noise electrons}} =$$

$$\frac{\int_{v1}^{v2} \left(\frac{\phi}{hv} \times t \times A \times QE\right) dv}{\int_{v1}^{v2} \sqrt{\left(\frac{\phi}{hv} \times t \times A \times QE\right)2 + \text{noise detector } 2 + \text{noise readout } 2} \, dv}$$

Where Φ is light power, hv is photon energy, A is area of detector and QE is quantum efficiency. For higher input signal, the SNR is proportional to $$\sqrt{\frac{\phi}{hv}}, \text{ where } \sqrt{\frac{\phi}{hv}} = \sqrt{\frac{\phi\lambda}{hc}},$$

and so integrating over a wide bandwidth, λ, will increase the SNR.

Performing differencing (electronic differencing as disclosed above), at 330, the MIT band data, such as, but not limited to, when modified, and the sub-band data to extrapolate the Reference band data when the sub-band is Reststrahlen band data or to extrapolate the Reststrahlen band data when the sub-band data is Reference band data. Differencing is performed via processing of the acquired filtered data. The difference can be calculated between each corresponding pixel in the two unique calibrated sets of data, and new pixel values used to generate imagery. With respect to the Reststrahlen signature, comparison of the Reference and Reststrahlen data enables separation of thermal and emissive components attributable to localized variations in scene content.

Figure 5:
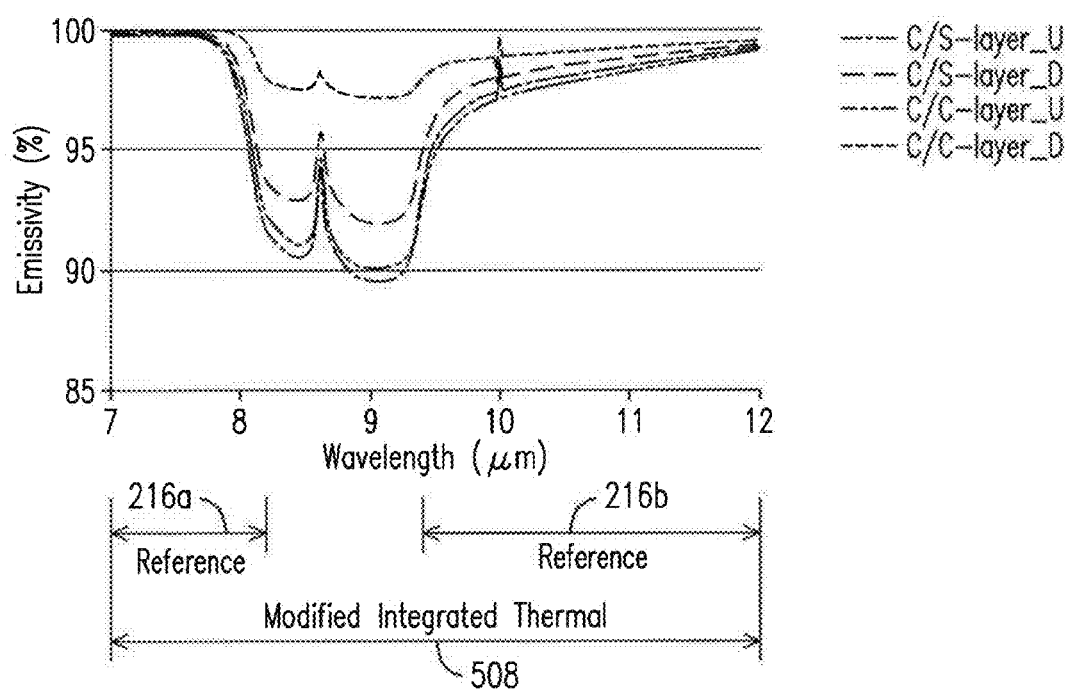
FIG. 5 shows a plot illustrating emissivity vs. wavelength of the Reststrahlen Effect on Disturbed Soil in combination with yet another Reference band and yet another Modified Integrated Thermal band in accordance with an embodiment.

FIG. 5 shows a plot illustrating emissivity vs. wavelength of the Reststrahlen Effect on Disturbed Soil in combination with a yet another Reference band and yet another Modified Integrated Thermal band. The two bands filtered are the Reference band 216a and 216b and the MIT band 508. The data collected may allow for analysis and imaging of Reststrahlen properties of ground and thermal properties in a scene. In this embodiment the Reststrahlen band data is computed or extrapolated by electronic differencing, with the one or more processors 120, from the Reference data captured from the Reference band 216a and 216b and the MIT data of the MIT band 508.

In an embodiment, the Reference band filter includes a single filter that rejects the Reststrahlen band 101 (FIG. 4A) but filters the full or nearly full bandwidth of MIT band 508, as seen in FIG. 5, wherein the Reference band filter may include a first band portion 216a configured to have a leading edge that corresponds to the leading edge of MIT band 508 and a trailing edge corresponding to a leading edge of the Reststrahlen band 101 (FIG. 4A). The MIT band 508 may include the full or nearly full bandwidth of the LWIR band spectrum. The Reference band filter may include a second band portion 216b having a leading edge that corresponds to the trailing edge of the Reststrahlen band 101, as seen in FIG. 5 and having a trailing edge correspond to the trailing edge of the MIT band 508.

In an embodiment, the Reference band filter may include a notch filter.

With respect to the illustration of FIG. 5, when the Reference band filter is used to acquire the Reference band data, the Reststrahlen band data is then computed. In an alternate embodiment, the system may be configured to acquire the Reststrahlen band data with a Reststrahlen band filter and compute a first band portion 216a and a second band portion 216b.

In the embodiment of FIG. 5, the leading edge of the Reference band portion 216a and the leading edge of the MIT band 508 are shown to have a cut-on of approximately 7 μm. In an embodiment, the MIT band 508 and the Reference band portion 216a may extend below the 7 μm cut-on into the medium-wave infrared (MWIR) thermal spectrum.

In view of the forgoing, the thermal infrared spectral region or spectrum may include a portion of the long wave infrared (LWIR) thermal band spectrum, the entire LWIR thermal band spectrum; or a combination of the (portion or entire) LWIR thermal band spectrum and a portion of the MWIR thermal band spectrum.

Figure 6:
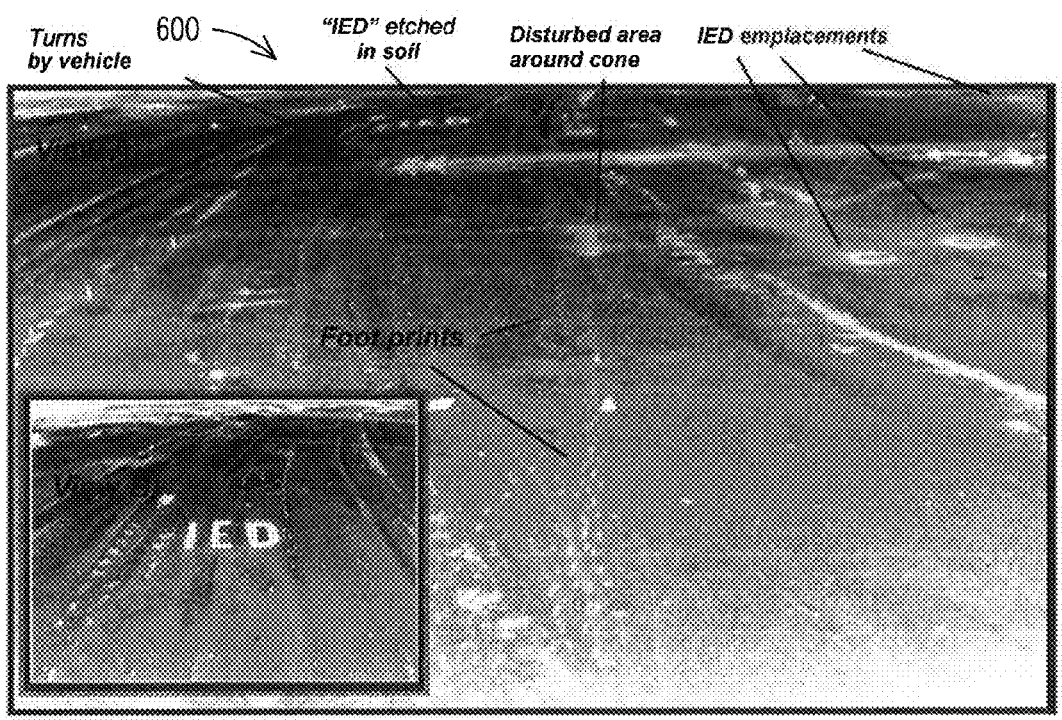
FIG. 6 shows a representation of anomalies identified by thermal and the Reststrahlen Effect on Disturbed Soil in an actual scene.

FIG. 6 shows a representation of anomalies identified by thermal and the Reststrahlen Effect on Disturbed Soil in an actual scene. The soil was disturbed purposely for illustration purposes. Several disturbances in the ground or soil were recognized. A first disturbance is where it was known a vehicle had made several turns or a plurality of turns. A second disturbance is where an individual etched, with a blade of a shovel, the letters "IED" into the ground surface. A third disturbance comprised detected footprints. A fourth disturbance was where a cone had been placed previously, including disturbance around where the cone was placed from human activity. A fifth disturbance was where IED emplacements had been located over an extended time period. A view in a bottom left hand corner illustrates the second-disturbance.

Embodiments described herein may be capable to improve on-the-move detection of Reststrahlen in combination with thermal signatures that enables improved detection of anomalies in a scene. Additionally, due to transmission cut-on for the MIT band filter (by way of non-limiting example, cut-on at the leading edge of the Reststrahlen band) and the Reference band (by way of non-limiting example, cut-on near the trailing edge of the Reststrahlen band), imagery has been found to be less vulnerable to reflective clutter in susceptible environments.

Additionally, by way of non-limiting example, Reststrahlen filtering may also less susceptible to variation that effect the silicate signature of soil (often seen on trailing edge of Reststrahlen signature), and the Reststrahlen filtering may not suffer from low SNR as do hyperspectral band techniques.

The embodiments may be mounted on, or used with, a vehicle, such a tank, manned or unmanned route clearance vehicle, or other military vehicle. In another embodiment, embodiments may be mounted on, or used with, a manned or unmanned air vehicle or lighter-than-air vehicle. Additionally, embodiments may be integrated with glasses or goggles, such as a head mounted display (HMD) device. In an embodiment, an augmented reality HMD) may use image data from one or more processors 120 to form computer generated image (CGI) data which is registered and combined with a real world view for the user to view such as without limitation in order to make a determination about a path to take.

Though embodiments are disclosed above with respect to IEDs and avoiding IEDs, the embodiments are also applicable to other uses. Such other uses include, but are not limited to, guiding movement or path of a (manned or unmanned) vehicle where a high amount of a component, such as, but not limited to, a silicate signature is present on a ground covering. The ground covering may comprises an amount of the silicate signature in a particular pattern, such but, but not limited to, where the pattern designates path. A vehicle comprising an embodiment disclosed herein may utilize the detected silicate signature to maintain the vehicle upon the path represented by the silicate signature.

In an embodiment, the systems 100 or 150 may be used in a controlled environment or activities of a planned or intentional design. The silicates or Reststrahlen effect can be deliberately controlled to effectuate differentiation states to convey differing information or signaling that are detectable by systems 100 and 150. By way of non-limiting example, the silicates may be dampened, attenuated and/or amplified in a controlled manner.

Based on what has been disclosed above, persons skilled in the art will recognize that an apparatus, such as a data processing system, including a CPU or one or more processors 120, memory, I/O, program storage, a connecting bus, and other appropriate components, could be programmed or otherwise designed to facilitate the practice of embodiments of the method. Such a system would include appropriate program means for executing the method.

Also, an article of manufacture, such as a pre-recorded disk, computer readable media, or other similar computer program product, for use with a data processing system, could include a storage medium and program means recorded thereon for directing the data processing system to facilitate the practice of the method.

Embodiments may also be described in the general context of computer-executable instructions, such as program modules, being executed by any device such as, but not limited to, a computer, designed to accept data, perform prescribed mathematical and/or logical operations usually at high speed, where results of such operations may or may not be displayed. Generally, program modules include routines, programs, objects, components, data structures, etc., that perform particular tasks or implement particular abstract data types. For example, the software programs that underlie embodiments can be coded in different programming languages, for use with different devices, or platforms. It will be appreciated, however, that the principles that underlie the embodiments can be implemented with other types of computer software technologies.

Moreover, those skilled in the art will appreciate that embodiments may be practiced with other computer system configurations, multiprocessor systems, microprocessor-based or programmable consumer electronics, minicomputers, mainframe computers, and the like. Embodiments may also be practiced in distributed computing environments where tasks are performed by processing devices located at different locations that are linked through at least one communications network. In a distributed computing environment, program modules may be located in both local and remote computer storage media including memory storage devices. In view of the above, a non-transitory processor readable storage medium is provided. The storage medium comprises an executable computer program product which further comprises a computer software code that may be executed on a processor.

In view of the above, a non-transitory processor readable storage medium is provided. The storage medium may comprise an executable computer program product which further comprises a computer software code that, when executed on one or more processors, causes the one or more processors to acquire MIT band data within a thermal detection bandwidth of a thermal infrared spectrum with an MIT band filter, and acquire a first sub-band data, using a sub-band filter, within a first sub-band bandwidth within the thermal detection bandwidth. The one or more processors is further caused to perform differencing of the MIT band data and the first sub-band data to compute or extrapolate a second sub-band data with one or more processors wherein 1) the first sub-band filter is configured to be one of a Reference band filter to capture Reference band data and a Reststrahlen band filter to capture Reststrahlen band data; and 2) the computed or extrapolated second sub-band data is Reference band data when the sub-band filter is a Reststrahlen band filter and the computed or extrapolated second sub-band data is Reststrahlen band data when the sub-band filter is a Reference band filter.

While various disclosed embodiments have been described above, it should be understood that they have been presented by way of example only, and not limitation. Numerous changes to the subject matter disclosed herein can be made in accordance with the embodiments disclosed herein without departing from the spirit or scope of the embodiments. In addition, while a particular feature may have been disclosed with respect to only one of several implementations, such feature may be combined with one or more other features of the other implementations as may be desired and advantageous for any given or particular application.

Thus, the breadth and scope of the subject matter provided herein should not be limited by any of the above explicitly described embodiments. Rather, the scope of the embodiments should be defined in accordance with the following claims and their equivalents.

Furthermore, while embodiments have been described with reference to various embodiments, it will be understood by those skilled in the art that various changes, omissions and/or additions may be made and equivalents may be substituted for elements thereof without departing from the spirit and scope of the embodiments. In addition, many modifications may be made to adapt a particular situation or material to the teachings of the embodiments without departing from the scope thereof. Therefore, it is intended that the embodiments not be limited to the particular embodiment disclosed as the best mode contemplated, but that all embodiments falling within the scope of the appended claims are considered. The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A system comprising:
an image sensor configured to receive scattered light from a scene in a thermal infrared spectral region;
a Modified Integrated Thermal (MIT) band filter to acquire MIT band data within a thermal detection bandwidth;
a sub-band filter to acquire a first sub-band data within a first sub-band bandwidth which is within the thermal detection bandwidth, the sub-band filter is a Reference band filter to capture Reference band data or a Reststrahlen band filter to capture Reststrahlen band data; and one or more processors configured to perform differencing of the MIT band data and the first sub-band data to compute a second sub-band data, the computed second sub-band data is Reference band data when the sub-band filter is the Reststrahlen band filter or the computed second sub-band data is Reststrahlen band data when the sub-band filter is the Reference band filter.

2. The system according to claim 1, wherein the one or more processors are further configured to generate spectral or thermal imagery of the scene from at least one localized variation in the scene attributable to a Reststrahlen effect or thermal phenomena.

3. The system according to claim 2, wherein the Reststrahlen effect or thermal phenomena are determined based on the Reststrahlen band data, the Reference band data and the MIT band data.

4. The system according to claim 2, further comprising a display for displaying information about the spectral imagery, thermal imagery or an alert.

5. A system according to claim 2, wherein the one or more processors configured to perform the differencing, is further configured to calculate between each corresponding pixel in two unique calibrated sets of data, and new pixel values used to generate the spectral or thermal imagery.

6. The system according to claim 1, further comprising a detector that creates a plurality of image pixels coupled to the one or more processors to generate an image based on the Reststrahlen band data, the Reference band data and the MIT band data.

7. The system according to claim 1, wherein the system is configured for insertion filtering comprising an opto-mechanical arrangement that provides insertion and removal of the MIT band filter and the sub-band filter in an optical path.

8. The system according to claim 1, wherein the system is configured for inline filtering and wherein the MIT band filter and the sub-band filter are in an optical path and filter simultaneously.

9. The system according to claim 1, wherein the sub-band filter comprises a detection bandwidth of approximately 8.2 µm to 9.4 µm for acquiring the sub-band filter data when the sub-band filter is the Reststrahlen band filter.

10. The system according to claim 1, wherein the sub-band filter comprises a detection bandwidth of approximately 9.4 µm to greater than 11 µm but less than or equal to 14 µm for acquiring the sub-band filter data When the sub-band filter is the Reference band filter.

11. A method comprising:
acquiring, by a Modified Integrated Thermal (MIT) band filter, MIT band data within a thermal detection bandwidth of a thermal infrared spectrum;
acquiring, by a sub-band filter, a first sub-band data within a first sub-band bandwidth which is within the thermal detection bandwidth; and
performing, by one or more processors, differencing of the MIT band data and the first sub-band data to compute a second sub-band data wherein the sub-band filter comprises a Reference band filter to capture Reference band data or a Reststrahlen band filter to capture Reststrahlen band data and the computed second sub-band data is Reference band data when the sub-band filter is the Reststrahlen band filter or the computed second sub-band data is Reststrahlen band data when the sub-band filter is the Reference band filter.

12. The method according to claim 11, further comprises generating spectral or thermal imagery of the scene from at least one localized variation in the scene attributable to a Reststrahlen effect or thermal phenomena with a processor.

13. The method according to claim 12, wherein the Reststrahlen effect or thermal phenomena are determined based on the Reststrahlen band data, the Reference band data and the MIT band data.

14. The method according to claim 11, further comprising displaying information about a spectral imagery, thermal imagery or an alert.

15. The method according to claim ii, further comprising inserting and removing the MIT band filter and the sub-band filter in an optical path from the scene sequentially.

16. The method according to claim 11, further comprising providing the MIT band filter and the sub-band filter in an optical path to filter simultaneously.

17. The method according to claim 11, wherein the sub-hand filter comprises a detection bandwidth of approximately 8.2 µm to 9.4 µm for acquiring the sub-band filter data when the sub-band filter is the Reststrahlen band filter.

18. The method according to claim 11, wherein the sub-band filter comprises a detection bandwidth of approximately 9.4 µm to greater than 11 µm but less than or equal to 14 µm for acquiring the sub-band filter data when the sub-band filter is the Reference band filter.

19. A non-transitory processor readable storage medium comprising executable computer program product which further comprises computer software code that, when executed on one or more processors, causes the one or more processors to:
process Modified Integrated Thermal (MIT) band data within a thermal detection bandwidth of a thermal infrared band spectrum from a MIT band filter;
process a first sub-band data within a first sub-band bandwidth which is within the thermal detection bandwidth from a sub-band filter, the sub-band filter is configured to be a Reference band filter to capture Reference band data or a Reststrahlen band filter to capture Reststrahlen band data; and
perform differencing of the MIT band data and the first sub-band data to compute a second sub-band data wherein the computed second sub-band data is Reference band data when the sub-band filter is the Reststrahlen band filter or the computed second sub-band data is Reststrahlen band data when the sub-band filter is the Reference band filter.

20. The non-transitory processor readable storage medium according to claim 19, when executed on one or more processors, causes the one or more processors to generate spectral or thermal imagery of the scene from at least one localized variation in the scene attributable to a Reststrahlen effect or thermal phenomena.

\* \* \* \* \*